United States Patent
Haeberlein et al.

(10) Patent No.: US 9,358,185 B2
(45) Date of Patent: Jun. 7, 2016

(54) POWDER COMPOSITION FOR AIR POLISHING THE SURFACE OF HARD DENTAL TISSUE

(71) Applicant: 3M INNOVATIVE PROPERTIES COMPANY, Saint Paul, MN (US)

(72) Inventors: Ingo R. Haeberlein, Weilheim (DE); Brenda Schmid, Markt Schwaben (DE); Aaron M. Pfarrer, Chicago, IL (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 14/407,789

(22) PCT Filed: Jun. 5, 2013

(86) PCT No.: PCT/US2013/044203
§ 371 (c)(1),
(2) Date: Dec. 12, 2014

(87) PCT Pub. No.: WO2013/191903
PCT Pub. Date: Dec. 27, 2013

(65) Prior Publication Data
US 2015/0125814 A1    May 7, 2015

(30) Foreign Application Priority Data

Jun. 18, 2012 (EP) .................................. 12172338

(51) Int. Cl.
*A61K 8/02* (2006.01)
*B24C 1/08* (2006.01)
(Continued)

(52) U.S. Cl.
CPC ............... *A61K 8/0241* (2013.01); *A61C 1/087* (2013.01); *A61C 17/022* (2013.01); *A61K 8/022* (2013.01);
(Continued)

(58) Field of Classification Search
CPC ........... A61K 8/022; A61K 8/24; A61K 8/25; A61K 8/362; A61K 8/44; A61K 8/0241; A61K 2800/412; A61C 1/087; A61C 17/022; A61Q 11/00; B24C 1/086
USPC ......................................... 451/36–40, 60, 446
See application file for complete search history.

(56) References Cited

U.S. PATENT DOCUMENTS 2,696,049 A * 12/1954 Black ..................... A61C 1/087
                                                  433/215
2,876,168 A *  3/1959 Broge ..................... A61K 8/24
                                                  424/57

(Continued)

FOREIGN PATENT DOCUMENTS

EP      00920482      10/1983
EP       2228175       9/2010
(Continued)

OTHER PUBLICATIONS

Sauro, "Dentine desensitization induced by prophylactic and air-polishing procedures: An in vitro dentine permeability and confocal microscopy", Journal of Dentistry, May 2010, vol. 38, No. 5, pp. 411-422.

(Continued)

*Primary Examiner* — George Nguyen (57) ABSTRACT

The invention is directed to a powder composition for air polishing the surface of hard dental tissue comprising a powder of water-soluble organic particles as component A, a powder of inorganic anti-caking agent(s) particles as component B and a powder of antihypersensitive acting particles as component C, the mean particle size of component A being in a range from about 15 to about 500 μm, the mean particle size of component C being in a range from about 0.5 to about 10 μm. The invention is also directed to a kit of parts comprising the powder composition and its use.

15 Claims, 2 Drawing Sheets

(51) Int. Cl.
*A61K 8/24* (2006.01)
*A61K 8/25* (2006.01)
*A61K 8/44* (2006.01)
*A61Q 11/00* (2006.01)
*A61C 1/08* (2006.01)
*A61C 17/022* (2006.01)
*A61K 8/362* (2006.01)

(52) U.S. Cl.
CPC ... *A61K 8/24* (2013.01); *A61K 8/25* (2013.01); *A61K 8/362* (2013.01); *A61K 8/44* (2013.01); *A61Q 11/00* (2013.01); *A61K 2800/412* (2013.01)

(56) References Cited

U.S. PATENT DOCUMENTS

| | | | | |
|---|---|---|---|---|
| 3,904,747 | A * | 9/1975 | Cordon | A61K 8/0241 424/49 |
| 3,972,123 | A | 8/1976 | Black | |
| 4,214,871 | A * | 7/1980 | Arnold | A61C 3/025 433/216 |
| 4,256,603 | A * | 3/1981 | Ibsen | A61C 13/0024 252/183.11 |
| 4,676,749 | A | 6/1987 | Mabille | |
| 5,203,698 | A * | 4/1993 | Blake | A61C 3/025 433/216 |
| 5,865,620 | A * | 2/1999 | Kutsch | B24C 11/00 433/88 |
| 6,126,444 | A | 10/2000 | Horiguchi | |
| 6,485,304 | B2 | 11/2002 | Beerstecher | |
| 6,648,644 | B1 | 11/2003 | Flemming | |
| 7,083,411 | B2 | 8/2006 | Flemmig | |
| 8,382,476 | B2 * | 2/2013 | Schulte | A61K 6/0011 433/215 |
| 2003/0008263 | A1 | 1/2003 | Cook | |
| 2006/0110339 | A1 * | 5/2006 | McGill | A61Q 11/00 424/49 |
| 2010/0297576 | A1 | 11/2010 | Donnet | |
| 2011/0117523 | A1 | 5/2011 | Cook | |
| 2011/0262507 | A1 * | 10/2011 | Spring | A46D 1/00 424/401 |
| 2011/0281238 | A1 | 11/2011 | Cook | |
| 2012/0027829 | A1 * | 2/2012 | Hashimoto | A61K 6/0017 424/401 |
| 2013/0017159 | A1 * | 1/2013 | Lippert | A61K 8/24 424/52 |
| 2013/0160785 | A1 * | 6/2013 | Thevenet | A61B 8/0241 132/200 |

FOREIGN PATENT DOCUMENTS

| | | | |
|---|---|---|---|
| GB | 2026359 | 2/1980 | |
| GB | WO 2009148907 A1 * | 12/2009 | A61C 3/025 |
| WO | WO 89-07932 | 9/1989 | |
| WO | WO 97-04741 | 2/1997 | |
| WO | WO 2004-075770 | 9/2004 | |
| WO | WO 2010-010360 | 1/2010 | |
| WO | WO 2011-123123 | 10/2011 | |

OTHER PUBLICATIONS

International Search report for PCT International Application No. PCT/US2013/044203 mailed on Jul. 22, 2013, 7 pages.

* cited by examiner

POWDER COMPOSITION FOR AIR POLISHING THE SURFACE OF HARD DENTAL TISSUE

CROSS REFERENCE TO RELATED APPLICATIONS

This application is a national stage filing under 35 U.S.C. 371 of PCT/US2013/044203, filed 5 Jun. 2013, which claims priority to European Application No. 12171228.1, filed 18 Jun. 2012, the disclosures of which are incorporated by reference in their entirety herein.

FIELD OF THE INVENTION

The invention relates to a powder composition, especially a dental powder composition comprising a powder mixture for the air polishing treatment of the surface of hard dental tissue.

BACKGROUND ART

Air polishing powders are typically based either on glycine or bicarbonate or carbonate. The solely intention of these powders is professional tooth cleaning.

Bicarbonate or carbonate based powders are, however, known to be quite abrasive for teeth and dental materials which limits their use in professional tooth cleaning.

To improve the use of air polishing, a powder, based on glycine, had been developed by 3M ESPE which is available on market as Clinpro™ Prophy Powder. Clinpro™ Prophy Powder can be used supra-gingivally (i.e. above the gum line) as well as sub-gingivally (i.e. below the gum line). In particular the latter is very unique because sub-gingival air polishing is absolutely contraindicated for abrasive powders.

US 2011/0117523 (Cook et al.) describes a dental composition comprising an air abrasive agent comprising a polyalkenoate acid and a propellant.

US 2010/029757 (Donnet et al.) relates to a powder for powder jet cleaning with a powder jet device, wherein the powder contains an alditol.

US 2011/0281238 (Cook et al.) refers to a method of removing an adhesion resin from a dental tooth comprising the step of contacting the dental tooth with a bioactive glass using an air abrasion system.

US 2003/0008263 (Cook et al.) relates to the use of a bioactive glass in the manufacture of an air abrasive agent for use in the treatment of dental hard tissue and pulpal disorders. Bioactive glass, however, seems to be quite damaging to sound dentin. Tests revealed an abrasion of more than about 1 $mm^3$, which is considered as too high.

U.S. Pat. No. 6,485,304 (Beerstecher et al.) describes a dental abrasive blasting or jet apparatus comprising a powder reservoir for storing a dental powder, a separate fluid receptacle, a branch line and a suction pump. The powder may contain aluminium oxide or dolomite.

U.S. Pat. No. 6,126,444 (Horiguchi et al.) relates to a plaque remover injected with water and compressed air comprising an abradant for removing dental plaque, etc. wherein the abradant comprises primarily granular polysaccharide.

U.S. Pat. No. 6,648,644 (Flemmig et al.) relates to the use of fine powders or powder mixtures for the preparation of an agent for powder-jet cleansing of dental root surfaces, wherein the powders or powder mixtures provide a density of no more than 2 $g/cm^3$ and or a mean particle size of no more than 45 μm.

However, there is still room for improvement especially with regard to the requirements to be fulfilled with respect to modern dental materials.

Patients and dentists nowadays have an increasing demand for compositions which are effective in cleaning the tooth surface and are essentially non-damaging to said surface.

Thus, there is still a need for an improved composition, which can be used as a tooth cleaning composition.

DESCRIPTION OF THE INVENTION

In particular, a composition is desired which can be applied easily, which is effective in cleaning the tooth surface, essentially non-damaging to the tooth surface and which may provide a therapeutical effect in addition, e.g. being suitable to close or protect open dentin tubules.

This object can be achieved by providing a powder composition for air polishing the surface of hard dental tissue (e.g. in the mouth of a patient) comprising
  a powder of water-soluble organic particles (e.g. glycin) as component A,
  a powder of anti-caking agent(s) particles (e.g. silica) as component B and
  a powder of antihypersensitive acting particles (e.g. TCP or TCP-FA) as component C,
  the mean particle size of component A being in a range from about 15 to about 500 μm,
  the mean particle size of component C being in a range from about 0.5 to about 10 μm.

Component C is different from component A and component B with respect to its chemical composition.

In another embodiment, the invention relates to a process of producing such a composition by mixing the powder components described in the text of the invention.

A further embodiment of the invention is directed to a process for treating the surface of hard dental tissue, the process comprising the step of applying the composition as described in any of the preceding claims to the surface of hard tissue with the aid of a powder-jet device The invention is also related to a kit of parts and a device suitable for applying the powder composition to the surface of a tooth.

Further, the invention is directed to a process for treating the surface of hard dental tissue, the process comprising the step of applying the composition as described in the present text to the surface of hard tissue with the aid of a powder-jet device.

Further, the invention is directed to the use of tricalciumphosphate (especially tricalcium phosphate coated with fumaric acid) for producing a powder composition for treating the surface of hard dental tissue, the powder composition being as described in the present text.

The invention is also directed to the use of a powder jet device for applying a powder composition as described in the present text for treating the surface of hard dental tissue.

DEFINITIONS

Unless defined otherwise, the below terms shall have the following meanings:

A "dental composition" means a composition which can and is to be used in the dental field. In this respect the composition should be not detrimental to the patient's health and thus free of hazardous and toxic components being able to migrate out of the composition.

A "liquid" means any solvent or liquid which is able to at least partially disperse or dissolve a component at ambient conditions (e.g. 23° C.). "Liquid" shall comprise every fluid, which can be transported by a powder jet device. Those liquids are mainly comprised of water.

A "particle" means a substance being a solid having a shape which can be geometrically determined. The shape can be regular or irregular. Particles can typically be analysed with respect to e.g. grain size (e.g. mean grain or particle size) and grain or particle size distribution.

The "mean particle size" of a powder can be obtained from the cumulative curve of the grain size distribution and is defined as the arithmetic average of the measured grain sizes of a certain powder mixture. Respective measurements can be done using commercially available granulometers (e.g. CILAS Laser Diffraction Particle Size Analysis Instrument).

The term "d90/μm" with regard to particle size measurement means that in 90% of the analyzed volume, the particles have a size below x μm. E.g., a particle size value of below 100 μm (d90) means that within the analyzed volume, 90% of the particles have a size below 100 μm.

"Mohs hardness" means the scale of hardness characterized by the scratch resistance, that is, the ability of a harder material to scratch a softer material.

On the Mohs scale, e.g. a pencil lead has a hardness of 1; a fingernail has hardness 2.5; a copper penny, about 3.5; a knife blade, 5.5; window glass, 5.5; steel file, 6.5; talc ($Mg_3Si_4O_{10}(OH)_2$) has a hardness of 1, gypsum ($CaSO_4 \cdot 2H_2O$) has a hardness of 2, calcit ($CaCO_3$) has a hardness of 3, fluorite ($CaF_2$) has a hardness of 4, apatit ($Ca_5(PO_4)_3(OH^-, Cl^-, F^-)$) has a hardness of 5; perlit has a hardness of 5.5; pumice has a hardness of 6.

A "powder" means a material composed of fine particles that are not cemented together and can be distributed using a powder jet device.

An "organic particle" means particles which contain covalently bonded carbon and hydrogen containing molecules.

An "inorganic particle" means particles which lack covalently bonded carbon and hydrogen atoms.

"Water-soluble" means that a substance as such is soluble in water at ambient conditions, comparable to a salt. That is, the substance is able to form individual molecules in water like glucose when dispersed in water at 23° C.

More specifically, according to the invention a substance or composition is defined as water-soluble, if less than about 10 wt.-% or less than about 5 wt.-% or less than about 2 wt.-% or less than about 1 wt.-% or less than about 0.1 wt.-% (with respect to the whole composition) of substance remains after the following procedure:
a) 800 mg of substance and 8.0 g demineralised water are placed into a centrifuge test tube of known weight.
b) The test tube is closed and shaken for 5 minutes.
c) The mixture is centrifuged with centrifugal acceleration (ac) of 9870 m/s² for 20 min.
d) The supernatant liquid is decanted.
e) The remaining precipitate is kept for 12 h at 23° C., followed by 12 h drying at 105° C. (+/−3.5° C.).
f) After cooling to room temperature in a dessicator the dry weight of the sample is determined and used for calculating the water soluble fraction.

A substance or composition is defined as water-insoluble, if more than about 90 or more than about 95 or more than about 98 wt.-% or more than about 99 wt.-% (with respect to the whole composition) of substance remains unsolved after the procedure described above.

An "antihypersensitive active agent" means a material being suitable to occlude or protect open dentin tubules.

A "powder jet device" means a device being suitable for applying a powder composition with the aid of gas (e.g. air), sometimes also together with a liquid (e.g. water).

"Hard dental tissue" means enamel, dentin and root cement.

"Air polishing" means an essentially non-abrading treatment of the surface of hard dental tissue with a powder composition which is applied with the aid of a powder jet device. During an air polishing treatment, the powder composition is applied together with a gas (typically air) and a liquid (typically water).

In contrast to "air polishing" the term "air abrasion" means the cutting or abrading of hard dental tissue with a powder composition which is applied with the aid of a powder jet device "Density" means specific density, i.e. mass per volume (e.g. $g/cm^3$). The mass is normally measured with an appropriate scale; the volume may be measured directly (from the geometry of the object) or by the displacement of a liquid. A very common instrument for the direct measurement of the density of a liquid is the hydrometer. A less common device for measuring fluid density is a pycnometer, a similar device for measuring the absolute density of a solid is a gas pycnometer. The density of a particular substance can also be taken from handbooks and lexica known to the person skilled in the art.

"Bulk density" or "powder density" is a property of powders and means the mass of many particles of the powders divided by the total volume they occupy. The total volume includes particle volume, inter-particle void volume and internal pore volume.

"Mass density" means the mass of a material per unit volume without considering inter-particle void volume and internal pore volume.

"Ambient conditions" within the meaning of the invention mean the conditions which the inventive solution is usually subjected to during storage and handling. Ambient conditions may, for example, be a pressure of about 900 to about 1100 mbar, a temperature of about −10 to about 60° C. and a relative humidity of about 10 to about 100%. In the laboratory ambient conditions are adjusted to about 23° C. and about 1013 mbar.

A composition or solution is "essentially or substantially free of" a certain component within the meaning of the invention, if the composition or solution does not contain said component as an essential feature. Thus, said component is not wilfully added to the composition or solution either as such or in combination with other components or ingredient of other components. A composition being essentially free of a certain component usually contains the component in an amount of less than about 1 wt.-% or less than about 0.1 wt.-% or less than about 0.01 wt.-% (or less than about 0.05 mol/l solvent or less than about 0.005 mol/l solvent or less than about 0.0005 mol/l solvent) with respect to the whole composition. Ideally the composition or solution does not contain the said component at all. However, sometimes the presence of a small amount of the said component is not avoidable e.g. due to impurities.

As used herein, "a", "an", "the", "at least one" and "one or more" are used interchangeably. The terms "comprises" or "contains" and variations thereof do not have a limiting meaning where these terms appear in the description and claims. Also herein, the recitations of numerical ranges by endpoints include all numbers subsumed within that range (e.g., 1 to 5 includes 1, 1.5, 2, 2.75, 3, 3.80, 4, 5, etc.).

Adding an "(s)" to a term means that the term should include the singular and plural form. E.g. the term "additive (s)" means one additive and more additives (e.g. 2, 3, 4, etc.).

DETAILED DESCRIPTION

It has been found that the composition described in the text of the invention fulfils the practitioners needs especially with regard to the balance between professional tooth cleaning and hypersensitivity treatment in one step properties without a clinical relevant loss of dentin.

The composition contains a powder additive (component C) which allows occlusion of dentinal tubules in parallel to the air polishing cleaning procedure.

According to the so-called hydrodynamic theory open accessible dentinal tubules may be the major origin for hypersensitivity sensation. Thus, occlusion of dentinal tubules may contribute to a pain relief.

If desired, occlusion of dentinal tubules can be evidenced by 3D microscopy and permeability measurements at e.g. bovine dentin samples.

The average diameter of dentin tubules is typically about 2 μm. This would require the use of a powder having an average particle size in that range, which, however, is a size which could cause difficulties when the powder is to be applied with a powder jet device.

It has been reported, that powders having a mean particle size below about 12 μm cannot be adequately transported in air polishing devices. Thus, the powder components typically need to have a particle size above 12 μm.

With the present powder composition this problem has been solved. The composition can be easily applied with the aid of a powder jet device, shows adequate cleaning performance on the surface of hard dental tissue and also addresses the issue of hypersensitivity.

Further, it was found that the hypersensitivity active additive is not changing the overall cleaning performance of the composition itself.

Tests for the measurement(s) are set out below in the Example section.

The powder components of the inventive powder composition can be characterized e.g. by mean particle size, density, powder transport rate, dentin abrasion, permeability and combinations of either of these parameters.

According to one embodiment, the powder composition as described in the present text can be characterized by at least one of the following features:
  Mean particle size of component A: below about 500 μm or below about 250 μm or below about 150 μm or in a range from about 15 to about 500 μm or in a range of about 15 to about 250 μm or in a range of about 15 to about 100 μm;
  Mean particle size of component C: from about 0.5 to about 10 μm or from about 0.5 to about 8 μm.

If desired, the mean particle size can be analysed with a granulometer (e.g. as described in more detail in the Example section below).

If the mean particle size of component A is either too large or too low, it might be difficult to adequately transport the composition with a powder jet device.

If the mean particle size of component C is too large, component C may not be able to efficiently occlude or protect open dentin tubules.

If the mean particle size of component C is too low the composition may be dusting.

According to one embodiment, the particle size distribution of the whole composition might be as follows:
  D90/μm: from about 30 to about 90 μm or from about 40 to about 80 μm
  D50/μm: from about 10 to about 50 μm or from about 20 to about 40 μm.
  D10/μm: from about 1 to about 10 μm or from about 2 to about 8 μm.
  Mean particles size: from about 10 to about 60 μm or from about 15 to about 50 μm.

According to one embodiment, the powder composition as described in the present text can be characterized by at least one of the following features:
  Mass density of component A: below about 2.5 g/cm$^3$ or below about 2.0 g/cm$^3$ or below about 1.8 g/cm$^3$ or from about 1.0 to about 2.5 g/cm$^3$ or from about 1.2 to about 2.0 g/cm$^3$;
  Mass density of component B: from about 1.2 to about 4 g/cm$^3$;
  Mass density of component C: from about 1.2 to about 4 g/cm$^3$.

The mass density of the components can be taken from text books or lexica known to the person skilled in the art. The mass density is often also referred to as crystal density in contrast to bulk or powder density.

If the density of components B and C is too high, the composition might become too abrasive.

If the density of component C is too low, it might become difficult for the particles to effectively enter the open dentin tubules as the overall impact of the powder particles is too low.

According to one embodiment, the powder composition as described in the present text can be characterized by at least one of the following features:
  Water solubility of component A: below about 10 wt.-% or below about 5 wt.-% or below about 2 wt.-% or below about 1 wt.-% (unsolved component A);
  Water solubility of component B: above about 90 wt.-% or above about 95 wt.-% or above about 98 wt.-% (unsolved component B);
  Water solubility of component C: above about 90 wt.-% or above about 95 wt.-% or above about 98 wt.-% or above about 99 wt.-% (unsolved component C).

If desired, the water solubility can be determined as described above.

The water solubility of component C is typically below the water solubility of component A. That is, component A can typically be dissolved in water quite easily, whereas it takes a longer period of time until component C dissolves in water.

The water solubility of component C should not be too high. The particles of component C should be capable to occlude or protect the dentin tubules. The occlusion of the dentin tubules should remain for a sufficient period of time. E.g. the dentin tubules should remain protected or occluded even after a tooth cleaning procedure using a tooth brush, a tooth paste and water. However, the water solubility of component C should, however, not be zero or close to zero, to prevent adverse effects to soft and hard dental tissues over time.

According to one embodiment, the powder composition as described in the present text can be characterized by at least one of the following features:

Molecular mass (Mr) of component A: from about 40 to about 1,000 or from about 50 to about 800 or from about 60 to about 600 (g/mol);

Molecular mass (Mr) of component B: from about 50 to about 100,000 or from about 50 to about 10,000 or from about 50 to about 1,000 (g/mol);

Molecular mass (Mr) of component C: from about 50 to about 1,000 or from about 50 to about 500 (g/mol).

In certain embodiments the inventive composition fulfils at least one or more, sometimes all of the following parameters:

Dentin abrasion: below about 0.2 or below about 0.18 or below about 0.15 or below about 0.1 mm$^3$/5 sec application time;

Powder transport rate: below about 10 or below about 8 or below about 5 g/min application time;

Permeability: permeability of dentinal tubules after treatment from about 5 to about 50% or from about 5 to about 30% in comparison to the permeability of untreated dentinal tubules (100%).

If desired, the dentin abrasion can be determined as follows: Dentin samples from bovine roots are treated with the inventive powder using a commercially available air polishing device for 5 sec with the nozzle of the air polishing device being held in a 60° angle and in a distance of 4.3 mm to the surface to be treated. The volume of the removed dentin is evaluated by microscopy.

A more detailed description can be found in the Example section.

If desired, the powder transport rate can be determined as follows: A commercially available air polishing device is used in accordance to the manufacturer's instruction for use without water supply. The powder transported in 30 sec is collected in a beaker filled with water. The weight difference is measured.

A more detailed description can be found in the Example section.

If desired, the permeability can be determined as follows: Human dentin samples are used to measure the water flow through the dentinal tubules. The water flow is measured before and after treatment. The lower the dentinal permeability, the higher the dentinal tubule occlusion is.

A more detailed description can be found in the Example section.

The nature and structure of Component A is not particularly limited unless the desired result cannot be achieved.

Component A is present in the composition in powder form. Component A comprises an organic powder.

The organic powder should be sufficiently water soluble. If the water solubility is too low, it can become difficult to smoothly remove the powder after a treatment of a patient. If the water solubility is too high, the powder may already dissolve during application with a powder jet device before the powder has reached the surface of the hard dental tissue. A water solubility as outlined above has been proven to be suitable.

The mass density of the organic powder should also be not too high. If the density of the organic powder is too high, the impact (e.g. impulse or momentum) caused by the organic powder when applied with pressure on the surface of hard dental tissue may cause an undesired abrasion of the hard dental tissue.

Examples of water-soluble particles, which can be used, include organic acids and their salts (including alkaline metal salts, alkaline earth metal salts, ammonium salts), amino acids and their salts (including alkaline metal salts, alkaline earth metal salts, ammonium salts), sugars (i.e. mono and di-saccharides), the respective alkaline metal salts, alkaline earth metal salts, ammonium salts and mixtures thereof.

Specific examples of organic acids and their salts include citric acid, ascorbic acid, ketoglutarsaure, pyruvic acid, lactic acid, phthalic acid, gluconic acid and mixtures thereof.

Specific examples of amino acids and their salts (especially the alkali metal salts) include glycine, alanine, glutamine, glutamic acid, asparagine, aspartic acid, serine, valine, leucine, iso-leucine, potassium glutamate, sodium glutamine and mixtures thereof.

Specific examples of sugars include xylitol, sorbitol, mannitol, erythritol, sorbitol, threitol, glucose, fructose, saccharose and mixtures thereof.

Component A typically functions as a cleaning agent for the surface of hard tissue to which the composition is applied.

The nature and structure of the powder(s) contained as component B is (are) not particularly limited unless the desired result cannot be achieved.

Component B is present in the composition in powder form. Component B is typically an inorganic powder. Component B is typically non-water soluble, however, water soluble anticaking agents can also be used, if desired.

Examples of anti-caking agents, which can be used, include fumed silica (e.g. Aerosil™, obtainable from e.g. Degussa Comp., Cab-o-Sil™ TS-530 (160-240 m$^2$/g), manufactured by Cabot Corporation, or HDKH™ (Wacker)), hollow or solid glass beads (e.g. S60™, iM 30K™ obtainable from 3M Company) and mixtures thereof.

Anti-caking agents used as component B may typically have a particle size d90/µm below about 75 µm, or below about 1 µm or even below about 20 nm.

An anti-caking agent may facilitate the dispensing or application of the composition out of the nozzle of a powder jet device, that is, to facilitate the powder transport during application.

If an anti-caking agent is present, it is typically present in a low amount. Amounts, found to be useful, include from about 0.001 to about 10 wt.-% or about 0.01 to about 5 wt.-% or about 0.1 to about 3 wt.-% with respect to the weight of the whole composition.

The nature and structure of component C is not particularly limited unless the desired result cannot be achieved.

Component C is present in the composition in powder form. Component C comprises an antihpyersensitive acting powder. The powder of component C is less water-soluble than the powder of component A.

Specific examples of the antihpyersensitive acting powder include phosphate releasing agents, hydroxylapatite, fluoroapatite, α-, β-, amorphous-tricalciumphosphate, calcium hydrogen phosphate, calcium oxalate, calcium carbonate, sodium fluoride, sodium mono flurorphosphate, stannous fluoride, N,N,N'-tris(2-hydroxyethyl)-N'-octadecylpropane-1,3-diamine dihydrofluoride, Ca(HCO$_3$)$_2$, NaHCO$_3$ and mixtures thereof.

Besides an antihypersensitive acting effect, some of the substances above may also act as fluoride releasing agent(s), in particular sodium fluoride, potassium fluoride, stannous fluoride, N,N,N'-Tris(2-hydroxyethyl)-N'-octadecyl-1,3-diaminopropan-dihydrofluorid (amine fluoride), sodium monofluorophosphate and mixtures thereof.

Explicit examples of the antihpyersensitive acting powder include α-tricalciumphosphate, β-tricalciumphosphate, amorphous tricalciumphosphate and mixtures thereof.

Component C functions as antihpyersensitive acting agent for the surface of hard tissue to which the composition is applied.

If desired, the particles of Component C can be surface treated.

Useful surface treatment agents include
organic acid(s) (e.g. organic acids like fumaric or maleic acid, and mixtures), thereof;
sodium lauryl sulphate and sodium dodecyl sulfate
and mixtures thereof.

A surface treatment can be beneficial in that undesired powder particle interactions may be prevented, in particular if fluoride containing powders are used.

An example of a particularly preferred powder additive as Component C is tricalciumphosphate coated with fumaric acid (TCP-FA). TCP-FA is commercially available from Indiana Nanotech, USA.

The particle size of the TCP-FA powder is typically from about 0.01 µm to about 50 µm or from about 0.05 µm to about 40 µm or from about 0.1 µm to about 30 µm.

The mean particle size is typically within a range from about 0.5 to 10 µm or from about 4 to 8 µm.

The d90/µm value is typically within a range from about 10 to about 15 µm. The d50/µm value is typically within a range from about 0.5 to about 8 µm. The d10/µm value is typically within a range from about 0.1 to about 2 µm.

It was found that it is sufficient for occluding and/or protecting open dentin tubules, if only a small amount of the particles of component C have a particle size below about 2 µm. There is no need that all particles of component C have a particle size in that range.

If used, TCP-FA is typically used in an amount from about 0.1 to about 15 wt.-% or from about 1 to about 10 wt.-% or from about 2 to about 8 wt.-% with respect to the weight of the whole composition. The measured abrasion at bovine dentin is typically below 0.2 mm$^3$ and thus meets the clinical requirement for sub-gingival use.

According to the test procedure for determining the water-solubility described in the present text, TCP-FA is considered an essentially water-insoluble substance.

Besides powder components A, B and C the inventive powder composition may contain further powder components as component D.

Either of the following further powder components (sometimes also referred to as adjuvants) can be present: colourant(s), hemostatic agent(s), pharmaceutical drug(s), anti-microbial agent(s) or mixtures thereof.

The term "agent(s)" means that either only one agent is present or different agents (e.g. 2 or 3) are present.

If desired, mixtures of those powder components can be present as well.

In a further embodiment, the composition may have a colour which may allow an easy detection in a patient's mouth (especially compared to oral tissue and/or tooth substance) and control whether after the treatment all residues of the composition have been removed from the sulcus. E.g., a blue, green or yellow colour may be suitable. Colouring of the composition can be achieved by incorporating colorants or pigments (organic and inorganic) into the composition.

Examples of colourants which can be used include red iron oxide 3395, Bayferrox 920 Z Yellow, Neazopon Blue 807 (copper phthalocyanine-based dye) or Helio Fast Yellow ER.

In a further embodiment the composition may comprise one or more hemostatic agents. Hemostatic agents (sometimes also referred to as astringent agents) that may be useful in assisting hemostasis include, but are not limited to oxides, chloride or sulphate salts of ferrum (e.g. ferric sulfate, ferric subsulfate, ferric chloride), aluminium (e.g. potassium aluminum sulfate, aluminum ammonium sulfate, aluminum sulfate, aluminum chlorohydrate, aluminum acetate) and zinc, polyphenols, ellag acid, permanganates (e.g. potassium permanganate), silver nitrate and hydrogen peroxide and mixtures thereof. One preferred class of hemostatics include aluminum compounds.

If a hemostatic agent is present, it is typically present in an amount of about 0.001 wt.-% to about 2 wt.-% or in an amount of about 0.01 wt.-% to about 1 wt.-% or in an amount of about 0.1 wt.-% to about 0.5 wt.-% with respect to the weight of the whole composition.

Pharmaceutical drugs which might contribute to a hemostatic effect include adrenaline, epinephrine, propylhexedrine, adrenochrom-monosemicarbazone propylgallat, tranexamic acid, etamsylate, batroxobin, thrombin, fibrin dressings.

Other useful pharmaceutical drugs include lidocain and articain.

In another embodiment, the dental composition comprises an anti-microbial agent. This might help reducing health risks for professionals in the dental offices and laboratories as well as for patients caused by bleeding prior impression taking caused by drilling or retracting the gingival cuff. It may reduce the risk of contamination of the patient having a wound as well as the risk of contamination of the impression taken, thus preventing contamination of dental professionals in the dental office as well as of the dental lab.

Preferred anti-microbial agents include: Hexitidin, Cetypyridiniumcloride (CPC), Chlorhexidin (CHX), Triclosan, stannous chloride, benzalkonium chloride, non-ionic or ionic surfactants (e.g. quarternary ammonium compounds), alcohols [monomeric, polymeric, mono-alcohols, poly-alcohols (e. g. Xylitol, Sorbitol), aromatic (e. g. phenol)], antimicrobial peptides (e. g. histatins), bactericins (e. g. nisin), antibiotics (e. g. tetracycline), aldehydes (e. g. glutaraldehyde) inorganic and organic acids (e. g. bencoic acid, salicylic acid, fatty acids) or there salts, derivative of such acids such as esters (e. g. p-hydroxy benzoate or other parabenes, lauricidin), enzymes (e. g. lysozyme, oxidases), proteins (e. g. enamel matrix protein, prolin rich proteins), fluoride, EDTA, essential oils (e. g. thymol). Several silver containing components are reported to have an antimicrobial effect, too.

Chlorhexidine and its derivatives (hereinafter referred to as CHX) are commercially available in water-based solutions (e.g. a 20% aqueous solution of CHX digluconate, CAS 18472-51-0) or as a pure compound or as a salt. As additive the pure Chlorhexidine compound (CAS 55-56-1) and CHX salts like CHX diacatate monohydrate (CAS 56-95-1) or CHX dihydrochloride (CAS 3697-42-5) are preferred.

CHX also seems to be especially suited as an additive due in part to its well-known and proven anti-microbial action against Gram positive and Gram negative microorganisms including the oral Streptococci and Lactobacilli. CHX is bacteriostatic for *Mycobaterium*. CHX is also active against yeasts including *Candida albicans* and viruses including HIV, HBV, HCV, Influenza- and Herpes virus. A further advantage of CHX is its low toxicity.

Useful combinations include chlorhexidine or derivatives thereof and aldehydes (glutaraldyde, phtaldehyde) and chlorhexidine or its derivatives and salts of phenolics or acids. It can also be preferred to use acid adducts of chlorhexidine or its derivatives like e.g., acetates, chlorides, nitrates, sulfates or carbonates.

If an anti-microbial agent is present, it is typically present in an amount of about 0.01 wt.-% to about 2 wt.-% or in an amount of about 0.1 wt.-% to about 1 wt.-% with respect to the weight of the whole composition.

The inventive powder composition typically contains the powder components in the following amounts:

Component A: at least about 50 wt.-% or at least about 70 wt.-% or at least about 90 wt.-% with respect to the whole composition.

Useful ranges for component A include from about 50 to about 98 wt-% or from about 60 to about 95 wt.-% from about 70 to about 93 wt-%.

Component B: utmost about 10 wt.-% or utmost about 5 wt.-% or utmost about 3 wt.-% with respect to the whole composition.

Useful ranges for component B include from about 0.001 to about 10 wt-% or from about 0.01 to about 5 wt-% from about 0.1 to about 1 wt-%.

Component C: at least about 0.1 wt.-% or at least about 0.5 wt.-% or at least about 1 wt.-% or at least about 5 wt.-% with respect to the whole composition.

Useful ranges for component C include from about 0.1 to about 15 wt.-% or from about 0.5 to about 10 wt.-% from about 1 to about 8 wt.-% or from about 5 to about 8 wt.-% with respect to the whole composition.

Component D: at least about 0 wt.-% or at least about 0.1 wt.-% or at least about 0.5 wt.-% with respect to the whole composition.

Useful ranges for component D include from about 0 to about 10 wt-% or from about 0.1 to about 8 wt-% from about 0.5 to about 5 wt-% or from about 1 to about 4 wt.-% with respect to the whole composition.

According to one embodiment the inventive composition contains the powder components in the following amounts:

Component A: from about 50 to about 98 wt-% or from about 70 to about 95 wt-%;

Component B: from about 0.001 to about 10 wt-% or from about 0.1 to about 2 wt-%;

Component C: from about 0.1 to about 15 wt-% or from about 1 to about 10 wt-%;

Component D: from about 0 to about 10 wt-% or from about 0.01 to about 8 wt-%.

If the amount of component A is too high, the amount of component C available for treating the hypersensitivity might not be sufficient.

If the amount of component A is too low, it could be difficult to achieve the desired cleaning effect.

If the amount of component B is too high, the composition might become too dusty.

If the amount of component B is too low, if could be difficult to achieve the desired flowability.

If the amount of component C is too high, the composition might become too abrasive and/or difficult to transport with a powder jet cleaning device.

If the amount of component C is too low, it could be difficult to achieve the desired therapeutical effect.

According to a particular embodiment, the invention is directed to a powder composition for air polishing the surface of hard dental tissue comprising a powder of water-soluble organic particles as component A, a powder of inorganic water-insoluble flowing agent(s) particles as component B, and a powder of water-insoluble antihypersensitive acting particles as component C, the mean particle size of component A being in a range from about 15 to about 500 μm, component A being present in an amount of at least about 80 wt.-% with respect to the weight of the whole composition, the mean particle size of powder component C being from about 0.5 to about 10 μm or from about 2 to about 8 μm, component C being present in an amount of less than about 10 wt.-% with respect to the weight of the whole composition.

According to a further particular embodiment, the powder composition for air polishing the surface of hard dental tissue (e.g. in the mouth of a patient) described in the present text comprises a powder of water-soluble organic particles as component A, the water-soluble particles being selected from amino acids and their salts, organic acids and their salts, sugars and mixtures thereof, a powder of inorganic anti-caking agent(s) particles as component B and a powder of antihypersensitive acting particles as component C.

the mean particle size of component A being in a range from about 15 to about 500 μm, the mean particle size of component C being in a range from about 0.5 to about 10 μm, the organic acids being selected from citric acid, ascorbic acid, ketoglutarsaure, pyruvic acid, lactic acid, phthalic acid, gluconic acid and mixtures thereof, the amino acids being selected from glycine, alanine, glutamine, glutamic acid, asparagine, aspartic acid, serine, valine, leucine, iso-leucine, potassium glutamate, sodium glutamine and mixtures thereof, the sugars being selected from xylitol, sorbitol, mannitol, erythritol, sorbitol, threitol, glucose, fructose, saccharose and mixtures thereof, the antihypersensitive acting particles being selected from phosphate releasing agent(s), hydroxylapatite, fluoroapatite, α-, β-, amorphous-tricalciumphosphate, tricalcium phosphate coated with an organic acid, calcium hydrogen phosphate, calcium oxalate, calcium carbonate, sodium fluoride, sodium mono fluorophosphate, stannous fluoride, N,N,N'-tris (2-hydroxyethyl)-N'-octadecylpropane-1,3-diamine dihydrofluoride, $Ca(HCO_3)_2$, $NaHCO_3$ and mixtures thereof.

According to a further particular embodiment, the powder composition for air polishing the surface of hard dental tissue described in the present text comprises a powder of water-soluble organic particles selected from amino acids, sugars, the respective alkaline metal salts, alkaline earth metal salts, ammonium salts and mixtures thereof as component A, silica powder as component B and phosphate releasing agent(s), hydroxylapatite, fluoroapatite, α-, β-, amorphous-tricalciumphosphate, tricalcium phosphate coated with an organic acid, calcium hydrogen phosphate, calcium oxalate, calcium carbonate, sodium fluoride, sodium mono fluorophosphate, stannous fluoride, N,N,N'-tris(2-hydroxyethyl)-N'-octadecylpropane-1,3-diamine dihydrofluoride, $Ca(HCO_3)_2$, $NaHCO_3$ and mixtures thereof as component C the mean particle size of component A being in a range from about 15 to about 500 μm, the mean particle size of component C being in a range from about 0.5 to about 10 μm.

According to a further particular embodiment, the powder composition for air polishing the surface of hard dental tissue described in the present text comprises a powder of water-soluble organic particles selected from amino acids the respective alkaline metal salts, alkaline earth metal salts, ammonium salts and mixtures thereof as component A, silica powder as component B and TCP or TCP-FA powder as component C, the mean particle size of component A being in a range from about 15 to about 500 µm, the mean particle size of component C being in a range from about 0.5 to about 10 µm.

According to a further particular embodiment, the powder composition for air polishing the surface of hard dental tissue (e.g. in the mouth of a patient) described in the present text comprises a powder of water-soluble organic particles selected from amino acids the respective alkaline metal salts, alkaline earth metal salts, ammonium salts and mixtures thereof as component A, silica powder as component B and TCP or TCP-FA powder as component C, the mean particle size of component A being in a range from about 15 to about 500 µm, the mean particle size of component C being in a range from about 0.5 to about 10 µm, component A being present in an amount from about 70 to about 95 wt-%, component B being present in an amount from about 0.1 to about 2 wt-%, component C being present in an amount from about 1 to about 10 wt-%.

The invention also relates to a process of producing the composition as described in the present text and to the product obtainable by such a process.

This process includes a mixing step, where the individual powder components are mixed.

If desired, the process can also comprise one or more sieving steps. Sieving steps may facilitate the adjustment of the desired particle size distribution.

The sequence of mixing the powder components is typically not critical, but it can be advantageous if the mixing is performed in the following order: Component A is provided first in powder form, then the powder of Component B is added and the composition mixed thoroughly, before Component D is added in powder form.

If desired, the components to be mixed can be milled first until an appropriate particle size is reached. Milling can be accomplished in a ball mill or air jet mill.

The invention also relates to a kit of parts.

The kit of parts comprises the powder composition as described in the present text and a device suitable for applying the powder composition to the surface of a tooth.

Such devices are well known to the practitioner and are currently used for cleaning tooth surfaces. The devices are sometimes also referred to as powder jet devices.

Typically, a powder jet device comprises a handpiece and a reservoir for storing the dental composition prior, during and after the use. The reservoir can be part of the handpiece or can be part of a separate basis station of the powder jet device.

The handpiece is typically reversible connectable via a (flexible) tube to the basis station of the powder jet device or to the dental chair unit equipped with a pressurized air/liquid unit. Thus, in certain embodiments, the handpiece is a part, which can be separated from the powder jet device and can be purchased independently from the powder jet device. The handpiece might comprise a reservoir for storing the dental composition described in the text of the invention.

Examples of powder jet devices, which can be used, include those described e.g. in GB 2 026 359 A, U.S. Pat. No. 3,972,123 or U.S. Pat. No. 4,676,749. The content of each of these documents with respect to the description of powder jet devices, handpieces and nozzles is herewith incorporated by reference and considered part of the description of the present invention.

Powder jet devices, which can be used and which are commercially available, include Airflow S1 (EMS S.A.), PROPHYflex 3 (KaVo Dental GmbH) and Cavitron PROPHY-JET (Dentsply DeTrey GmbH).

If desired, the kit of parts may contain an instruction of use. The instruction of use typically provides the practitioner with hints and advices how to best apply the composition.

The invention is also directed to a process for treating the surface of hard dental tissue, the process comprising the step of applying the composition as described in the present text to the surface of hard tissue with the aid of or by using a powder-jet device, especially for a period of time sufficient to a) clean the surface of the hard dental tissue and b) to at least partially occlude open dentin tubules.

The invention is also directed to a process for treating the surface of hard dental tissue, the process comprising the step of applying the composition as described in the present text to the surface of hard tissue with the aid of a powder-jet device.

A further aspect of the invention is directed to the use of TCP-FA for producing a powder composition for treating the surface of hard dental tissue, the powder composition being as described in the present text.

A further aspect of the invention is directed to the use of a powder jet device for applying a powder composition for treating the surface of hard dental tissue, the powder composition being as described in the present text.

The inventive powder composition is typically filled in a powder reservoir of a powder jet device.

The composition is typically applied using gas or a gas stream. The nature of the gas which can be used is not particularly limited unless an unwanted reaction between the dental composition to be applied and the gas stream takes place. Moreover, gases which might be detrimental to the patient's health or might be damaging to the powder jet device are typically not used.

Gas which can be used include air, nitrogen, argon, carbon dioxide or mixture of one or more of these gases.

The pressure of the gas is typically in a range of about 0.5 to about 10 bar or of about 1 and about 8 bar or of about 2 and about 6 bar or 3 to about 5 bar.

The dental composition can be applied together with a liquid, if desired. The nature of the liquid which can be used is not particularly limited, either, unless an unwanted reaction between the dental composition to be applied and the liquid takes place. Moreover, liquids which might be detrimental to the patient's health or might be damaging to the powder jet device are typically not used.

Liquids which can be used include water, alcohols, especially low boiling alcohols including ethanol, and ketones including acetone and mixtures of one or more of these liquids. Typically, water is preferred.

If a liquid is used, the liquid might be able to partially or fully dissolve some of the powder components being present in the dental composition, that is, at least a part of the composition might be soluble in the liquid. The liquid may also prevent the formation of undesired dust during the application of the composition.

If the powder jet device is used to apply a liquid and the composition, the liquid can be applied either together with the gas or separately from the gas. In the latter case, the handpiece of the powder jet device has typically different orifices in the nozzle, one orifice for the gas, one orifice for the powder and one orifice for the liquid.

According to one embodiment, the composition does not contain bioactive glass, like the material described e.g. WO 2010/010360 or US 2003/0008263. US 2003/0008263 defines the term "bioactive glass" as a glass or ceramic material comprising Si-oxide or Si-hydroxide which is capable of developing a surface calcium phosphate/hydroxyl-carbonate apatite layer in the presence of an aqueous medium, so producing a biologically useful response. Bioglass is said to have a Vicker's Hardness of about 458 (+/−9.4).

According to one embodiment, the composition does not contain polyalkenoate acid(s), like the material described e.g. US 2011/0117523. (Cook et. al.)

As the powder composition is typically applied by using a powder jet device, the powder composition described in the present text does not contain solvents or liquids. The addition of liquids or solvents to the powder composition would result in a slurry or pasty composition. In such a state the composition cannot be applied with a powder jet device.

Typically, the inventive composition does not contain components which are damaging to the surface of dental hard tissues to be treated.

In this respect, certain embodiments of the dental composition do not contain more than about 10 wt.-% abrasive particles. Common to most of these substance (i.e. abrasive particles) is typically a comparable high hardness, e.g. above about Mohs 4 or above about 5 or above about 300 or 400 Vicker's Hardness.

Abrasive particles which are typically used in dentifrices and which might be regarded as damaging include, perlite, sand or quartz, ground glass, silicon carbide, alumina, ilmenite ($FeTiO_3$), zircon oxide, zircon silicate, topaz, $TiO_2$, precipitated lime, chalk, flour of pumice, zeolites, talcum, kaolin, kieselguhr, aluminium oxide, and silicates.

Furthermore, all components used in the composition of the invention should be biocompatible, that is the composition should not produce a toxic, injurious, or immunological relevant response in living tissue.

The complete disclosures of the patents, patent documents, and publications cited herein are incorporated by reference in their entirety as if each were individually incorporated.

Examples

Unless otherwise indicated, all parts and percentages are on a weight basis, all water is de-ionized water or tap water (for use with powder jet devices). Further, unless otherwise indicated, density usually means specific density and is typically taken from the respective manufacturer specification or literature available to the skilled person in the art. Moreover, unless otherwise indicated all Experiments were conducted at ambient conditions (23° C.; 1013 mbar).

Measurements
Particle Size/Particle Size Distribution

The mean particle size (MPZ) was determined using a commercially available granulometer (Laser Diffraction Particle Size Analysis Instrument, MASERSIZER 2000; Malvern Comp.) according to the instruction of use provided by the manufacturer. The values determined are referred to as volume weighted mean value (m).

Powder Transport Rate

The powder transport rate data was obtained as follows: A commercially available air polishing device was used (EMS Airflow™ Handy 2 device; EMS S.A. Company) in accordance to the manufacturer's instruction for use without water supply. The powder transported in 30 sec was collected in a beaker filled with water. The weight difference was measured.

Dentin Abrasion

Bovine tooth root was cleaned, sewed and sandpapered until the surface was smooth. The root was embedded in a brass holder filled with putty (3M ESPE Express impression material) and covered with a brass lid to obtain a smooth surface. After the setting of the embedding material, the bovine root was treated with the composition wherein the nozzle of the air polishing device was held in a 60° angle. The root was treated for 5 sec. The treatment distance was about 4.3 mm.

The volume of the generated defects was calculated with a Keyence CLSM microscope with a 10-fold objective. If the defect was greater than the range of the 10-fold objective an assembled image was generated. The defect was calculated in $mm^3$ with the VK Analyser 2.4 Software out of an average of a 5-fold measurement.

Permeability Measurement

The data for determining the permeability was obtained as follows: Crown segments were cut from extracted human molars. The dentine disks were about 2-3 mm think. The surfaces of the dentin disks were treated with a 320 grit abrasive paper and etched for 2 to 5 sec with 37% phosphoric acid. The dentin disks were connected to a luer-lock connection from the pulp side of the disk. These were attached to a tube filled with a 10 mM fluorescein solution under 70 cm $H_2O$ pressure.

The dentin disks were placed in 1 ml phosphate buffered saline (PBS) solution. The fluorescein solution was allowed to pass through the dentin for 3×5 min. The amount of fluorescein solution that flew into the PBS solution was measured at 488 nm. The permeability of the dentin sample was measured before and after powder treatment.

Permeability measurements are suitable to determine the decrease of fluid flow through dentinal tubules in response to an air polishing treatment with the inventive formulation.

Microscopic Images

The microscopic images were obtained with a CLSM from KEYENCE Corporation (VK-9700) as follows: Crown segments were cut from extracted human molars. The dentine disks were about 2-3 mm thick. The surfaces of the dentin disks were treated with a 320 grit abrasive sandpaper and etched for 2 to 5 sec with 37% phosphoric acid.

The dentinal surfaces were inspected before and after treatment with the inventive composition (1 sec treatment using a commercial available powder jet device; Keyence microscope).

With a 3D surface analysis, by scanning the surface with a 406 nm laser, the occlusion of dentinal tubules can be (visually) proven; see FIG. 1a, 1b, 2a, 2b.

Compositions
Abbreviations

TABLE 1

| Name | Description | Availability |
|---|---|---|
| Glycine; CAS 56-40-6 | Amino acid | Fluka, Sigma-Aldrich |
| TCP; CAS 7758-87-4 | Tricalcium phosphate | Fluka, Sigma-Aldrich |
| HDKH | Pyrogenic silica | Wacker; DE |
| Fumaric acid; CAS 110-17-8 | Organic acid | Fluka, Sigma-Aldrich |
| TCP-FA | Tricalcium phosphate coated with fumaric acid | Indiana Nanotec; USA |

Preparation of Compositions Add

The following compositions were prepared:

TABLE 2

|  | Sample 1* | Sample 2 | Sample 3 | Sample 4 |
|---|---|---|---|---|
| Component A | 99.64% glycine MPZ: 29 μm | 89.64% glycine MPZ: 29 μm | 92.14% glycine MPZ: 29 μm | 94.64% glycine MPZ: 29 μm |
| Component B | 0.36% HDKH | 0.36% HDKH | 0.36% HDKH | 0.36% HDKH |
| Component C | — | 10% TCP-FA MPZ: 6 μm | 7.5% TCP-FA MPZ: 6 μm | 5% TCP-FA MPZ: 6 μm |

*Clinpro ™ Prophy Powder (3M ESPE)

Method of Application

The powder jet device used for the application of the composition was an EMS Airflow™ Handy 2 device (available from EMS S.A. Company). The device was equipped with a nozzle having two orifices, one for the powdery substance to be applied together with gas and one for liquid.

The respective powder or mixture of powders was filled into the powder reservoir of the powder jet device. The gas used for the application of the powder was air (gas pressure: 3 to 6 bar). The liquid, which was applied simultaneously with the powder, was water.

Results

The compositions described above were tested with respect to powder transport, dentin abrasion and reduction in permeability. The test results are given in Table 3.

TABLE 3

| Sample | Powder Transport [g/min] | Dentin Abrasion [mm$^3$] | Reduction in Permeability after treatment [%] |
|---|---|---|---|
| 1* | 2.74 | 0.023 | 30.0 |
| 2 | 2.25 | 0062 | 81.8 |
| 3 | 1.99 | 0.052 | 76.7 |
| 4 | 2.02 | 0.060 | 53.8 |

What can be seen is that by adding an antihypersensitive acting agent (e.g. TCP-FA) to a powder composition, the permeability through dentin tubules can be reduced while keeping the dentin abrasion rate still in an acceptable range. Further, it was found that this effect can be enhanced, if the amount of antihypersensitive acting agent used is increased.

Figure 1A:
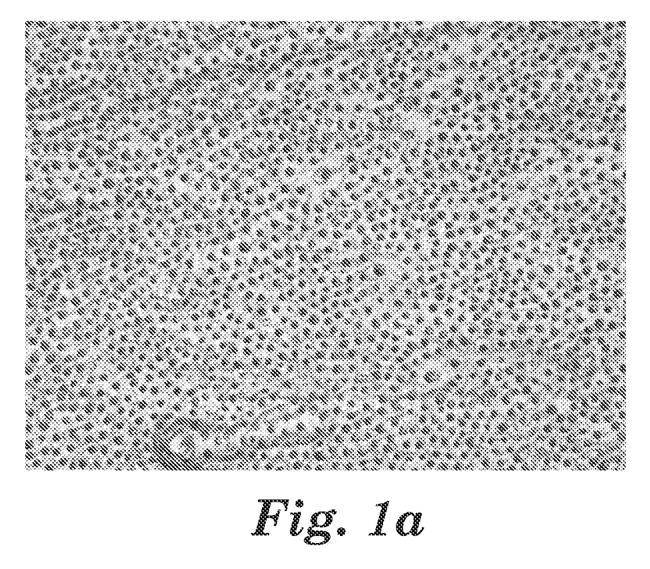
FIG. 1a shows a microscopic image of the surface of hard dental tissue before treatment with the inventive composition.
Figure 1B:
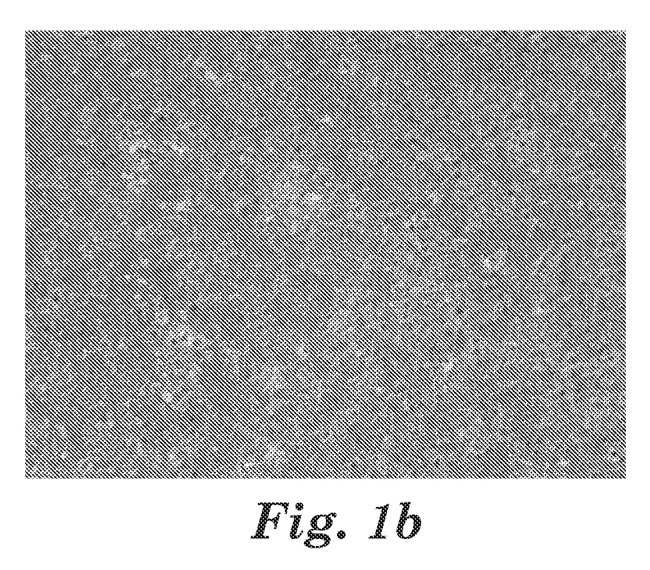
FIG. 1b shows a microscopic image of the surface of hard dental tissue after treatment with the inventive composition.

In the figures microscopic images of the surface of hard dental tissue can be seen before (FIG. 1a) and after treatment with the inventive composition (FIG. 1b).

Figure 2A:
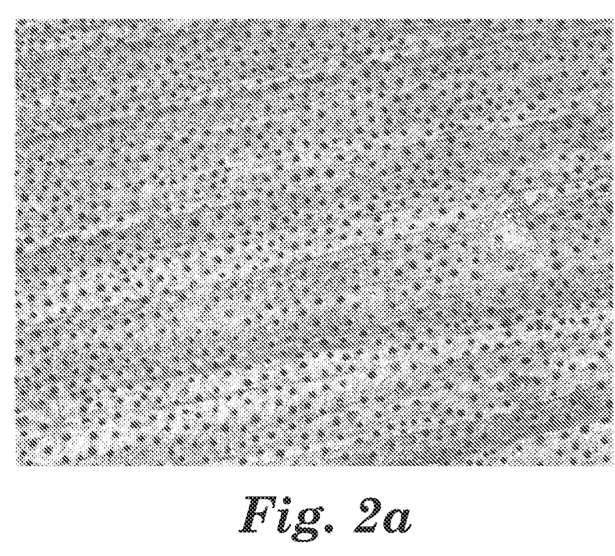
FIG. 2a shows a microscopic image of the surface of hard dental tissue before treatment with Clinpro™ Prophy Powder (3M ESPE).
Figure 2B:
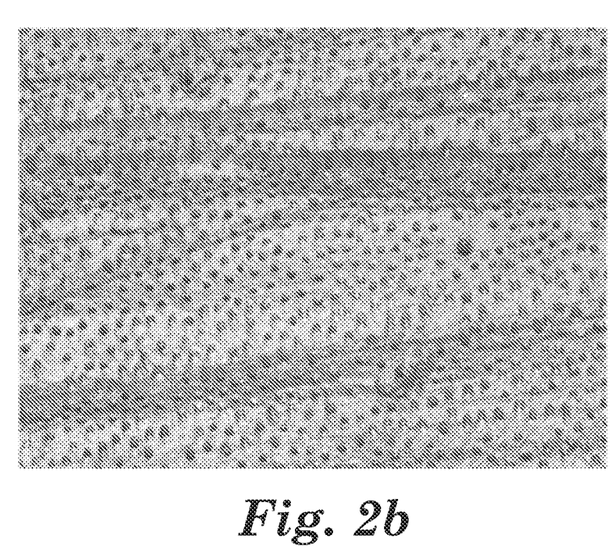
FIG. 2b shows a microscopic image of the surface of hard dental tissue after treatment with Clinpro™ Prophy Powder (3M ESPE).

In the further figures microscopic images of the surface of hard dental tissue can be seen before (FIG. 2a) and after treatment with the commercially available product Clinpro™ Prophy Powder (3M ESPE) (FIG. 2b).

The images were taken with a CLSM KEYENCE Corporation VK-9700 Series Microscope using a 20× and a 50× objective lens.

The hard dental tissue has been prepared as follows: Crown segments were cut from extracted molars. The human dentine disks were about 2-3 mm think. The surfaces of the dentin disks were treated with 320 grit abrasive sandpaper and etched for 2 to 5 sec with 37% phosphoric acid.

The dentinal surfaces were observed with a Keyence microscope before and after treatment with the inventive composition for 1 sec using a commercial available powder jet device.

The surface of the hard dental tissue has been treated with the respective composition applying the following conditions: treatment period: 1 sec; pressure: 4.0 bar; distance: 4.3 mm; using the device EMS Airflow™ S1 (EMS Corp.).

The invention claimed is:

1. A powder composition comprising:
   a powder of water-soluble organic particles as component A,
   a powder of inorganic anti-caking agent(s) particles as component B and
   a powder of antihypersensitive acting particles as component C,
   the mean particle size of component A being in a range from about 15 to about 500 μm,
   the mean particle size of component C being in a range from about 0.5 to about 10 μm.

2. The powder composition as described in claim 1 being characterized by at least one of the following features:
   Mass density of component A: below about 2.5 g/cm$^3$,
   Mass density of component B: from about 1.2 to about 4.0 g/cm$^3$,
   Mass density of component C: from about 1.2 to about 4.0 g/cm$^3$.

3. The powder composition as described in claim 1 being characterized by at least one of the following features:
   Water solubility of component A being greater than the water solubility of component C;
   Water solubility of component B: none.

4. The powder composition as described in claim 1 being characterized by at least one of the following features:
   Amount of component A: from about 50 to about 98 wt.-%,
   Amount of component B: from about 0.001 to about 10 wt.-%,
   Amount of component C: from about 0.1 to about 15 wt.-%, wt.-% with respect of the weight of the whole composition.

5. The powder composition as described in claim 1, wherein component A is selected from organic acids, amino acids, sugars, the respective alkaline metal salts, alkaline earth metal salts, ammonium salts and mixtures thereof.

6. The powder composition as described in claim 1, wherein component B is selected from fumed silica, hollow or solid glass beads and mixtures thereof.

7. The powder composition as described in claim 1, wherein component C is selected from phosphate releasing agents, hydroxylapatite, fluoroapatite, α-, β-, amorphous-tricalciumphosphate, tricalciumphosphate coated with an organic acid, calcium hydrogen phosphate, calcium oxalate, calcium carbonate, sodium fluoride, sodium mono fluorophosphate, stannous fluoride, N,N,N'-tris(2-hydroxyethyl)-N'-octadecylpropane-1,3-diamine dihydrofluoride, Ca(HCO$_3$)$_2$, NaHCO$_3$ and mixtures thereof.

8. The powder composition as described in claim 1,
   component A being selected from amino acids, sugars, the respective alkaline metal salts, alkaline earth metal salts, ammonium salts and mixtures thereof,
   component C being selected from phosphate releasing agents, hydroxylapatite, fluoroapatite, α-, β-, amorphous-tricalciumphosphate, tricalciumphosphate coated with fumaric acid, calcium hydrogen phosphate, calcium oxalate, calcium carbonate, sodium fluoride, sodium mono fluorophosphate, stannous fluoride, N,N,N'-tris(2-hydroxyethyl)-N'-octadecylpropane-1,3-diamine dihydrofluoride, Ca(HCO$_3$)$_2$, NaHCO$_3$ and mixtures thereof.

9. The powder composition as described in claim 1 comprising
- a powder of water-soluble organic particles as component A, the water-soluble particles being selected from amino acids and their salts, organic acids and their salts, sugars and mixtures thereof,
- a powder of inorganic anti-caking agent(s) particles as component B and
- a powder of antihypersensitive acting particles as component C, the organic acids being selected from citric acid, ascorbic acid, ketoglutarsaure, pyruvic acid, lactic acid, phthalic acid, gluconic acid and mixtures thereof, the amino acids being selected from glycine, alanine, glutamine, glutamic acid, asparagine, aspartic acid, serine, valine, leucine, iso-leucine, potassium glutamate, sodium glutamine and mixtures thereof, the sugars being selected from xylitol, sorbitol, mannitol, erythritol, sorbitol, threitol, glucose, fructose, saccharose and mixtures thereof, the antihypersensitive acting particles being selected from phosphate releasing agent(s), hydroxylapatite, fluoroapatite, α-, β-, amorphous-tricalciumphosphate, tricalcium phosphate coated with an organic acid, calcium hydrogen phosphate, calcium oxalate, calcium carbonate, sodium fluoride, sodium mono fluorophosphate, stannous fluoride, N,N,N'-tris(2-hydroxyethyl)-N'-octadecylpropane-1,3-diamine dihydrofluoride, $Ca(HCO_3)_2$, $NaHCO_3$ and mixtures thereof.

10. The powder composition as described in claim 1 further comprising one or more adjuvants as component D selected from colourant(s), hemostatic agent(s), pharmaceutical drug(s), anti-microbial agent(s), and mixtures thereof.

11. Kit of parts comprising:
  the powder composition as described in claim 1 and
  a device suitable for applying the powder composition to the surface of a tooth.

12. A method of producing a powder composition to be used for air-polishing the surface of hard dental tissue, the method comprising the step of mixing components A and B with (i) tricalciumphosphate or (ii) tricalcium phosphate coated with an organic acid, components A and B being as described in claim 1.

13. Use of a powder jet device for applying a powder composition for treating the surface of hard dental tissue, the powder composition being as described in claim 1.

14. A process for treating the surface of hard dental tissue, the process comprising the step of applying the composition as described in claim 1 to the surface of hard dental tissue with the aid of a powder-jet device.

15. The process as described in claim 14 being characterized by at least one of the following parameters:
  Dentin abrasion after treatment: below about 0.2 $mm^3$;
  Powder transport rate: at least about 1 g/min;
  Dentin tubuli permeability after treatment: from about 5 to about 50%.

* * * * *